(12) United States Patent
Barak et al.

(10) Patent No.: US 8,848,185 B2
(45) Date of Patent: Sep. 30, 2014

(54) OPTICAL SYSTEM AND METHOD FOR MEASURING IN THREE-DIMENSIONAL STRUCTURES

(75) Inventors: Gilad Barak, Rehovot (IL); Boaz Brill, Rehovot (IL)

(73) Assignee: Nova Measuring Instruments Ltd., Rehovot (IL)

( * ) Notice: Subject to any disclaimer, the term of this patent is extended or adjusted under 35 U.S.C. 154(b) by 0 days.

(21) Appl. No.: 13/980,504

(22) PCT Filed: Jan. 18, 2012

(86) PCT No.: PCT/IL2012/050014
§ 371 (c)(1),
(2), (4) Date: Jul. 18, 2013

(87) PCT Pub. No.: WO2012/098550
PCT Pub. Date: Jul. 26, 2012

(65) Prior Publication Data
US 2013/0308131 A1   Nov. 21, 2013

Related U.S. Application Data

(60) Provisional application No. 61/433,993, filed on Jan. 19, 2011.

(51) Int. Cl.
| | |
|---|---|
| G01J 4/00 | (2006.01) |
| G01B 11/02 | (2006.01) |
| G01B 11/22 | (2006.01) |
| G01N 21/956 | (2006.01) |
| G01N 21/95 | (2006.01) |
| H04L 25/02 | (2006.01) |
| G01B 11/12 | (2006.01) |
| G01N 21/88 | (2006.01) |
| H04L 27/26 | (2006.01) |
| H01L 21/66 | (2006.01) |

(52) U.S. Cl.
CPC .... *G01N 21/9501* (2013.01); *G01N 2021/8822* (2013.01); *H04L 27/2655* (2013.01); *G01B 11/02* (2013.01); *G01B 11/22* (2013.01); *G01N 21/956* (2013.01); *H04L 27/2607* (2013.01); *H04L 25/0222* (2013.01); *H04L 25/0226* (2013.01); *H04L 25/0216* (2013.01); *G01B 2210/56* (2013.01); *G01B 11/12* (2013.01); *H01L 22/12* (2013.01)
USPC ........................................................ 356/369

(58) Field of Classification Search
USPC .................................................. 250/559.09
See application file for complete search history.

(56) References Cited

U.S. PATENT DOCUMENTS

| | | |
|---|---|---|
| 5,048,968 A | 9/1991 | Suzuki |
| 5,208,648 A | 5/1993 | Batchelder et al. |
| 6,690,024 B1 | 2/2004 | Funaoka et al. |

(Continued)

FOREIGN PATENT DOCUMENTS

WO    2009074984 A2    6/2009

*Primary Examiner* — Tri Ton
*Assistant Examiner* — Willie Merrell, II
(74) *Attorney, Agent, or Firm* — Browdy and Neimark, PLLC (57) ABSTRACT

An optical system is presented for use in measuring in patterned structures having vias. The system is configured and operable to enable measurement of a via profile parameters. The system comprises an illumination channel for propagating illuminated light onto the structure being measured, a detection channel for collecting light returned from the illuminated structure to a detection unit, and a modulating assembly configured and operable for implementing a dark-field detection mode by carrying out at least one of the following: affecting at least one parameter of light propagating along at least one of the illumination and detection channels, and affecting propagation of light along at least the detection channel.

15 Claims, 7 Drawing Sheets

(56) References Cited

U.S. PATENT DOCUMENTS

| | | |
|---|---|---|
| 7,379,185 B2 | 5/2008 | Borden et al. |
| 2003/0053059 A1 | 3/2003 | Mishima et al. |
| 2003/0147069 A1 | 8/2003 | Li et al. |
| 2003/0223087 A1 | 12/2003 | Sasazawa et al. |
| 2005/0057755 A1 | 3/2005 | Johnson et al. |
| 2005/0125184 A1 | 6/2005 | Ye et al. |
| 2006/0132806 A1 | 6/2006 | Shchegrov et al. |
| 2007/0232874 A1 | 10/2007 | Ince |
| 2008/0055609 A1 | 3/2008 | Finarov et al. |
| 2009/0128824 A1 | 5/2009 | Leitgeb et al. |
| 2010/0271473 A1 | 10/2010 | Aiko et al. |
| 2010/0271621 A1 | 10/2010 | Levy et al. |

FIG. 1

(GENERAL ART)

OPTICAL SYSTEM AND METHOD FOR MEASURING IN THREE-DIMENSIONAL STRUCTURES

FIELD OF THE INVENTION

The present invention is generally in the field of optical measurement techniques, and relates to an optical system and method for measuring in three-dimensional structures, such as semiconductor wafers.

BACKGROUND OF THE INVENTION

As semiconductor technology progresses, shrinking device dimensions has become an increasingly complex task. One approach to overcome these difficulties is by using vertical integration of multiple semiconductor devices (chips). This allows larger number of devices per unit (e.g. in memory applications), as well as integration of chips of different functionality thus allowing better performance of a hybrid system (e.g. sensor, processor and memory).

One method under development for vertical integration is based on Through Silicon Via (TSV). TSV is a vertical electrical connection (via) passing completely through a silicon wafer or die. TSV is a high performance technique to create 3D packages and 3D integrated circuits (as compared to its alternatives such as package-on-package), because the density of vias is substantially higher and the length of the connections is shorter. According to TSV, conducting pillars are formed within a silicon substrate, later to be used for contacting successive chips. To connect electrically the components in different layers, TSV technology is used to provide the electrical interconnect and to provide mechanical support. In TSV technology, a via is fabricated in a silicon chip with different active integrated circuit devices or other devices fabricated by a semiconductor process, and the via is filled with metal such as Cu, Au, W, solders, or a highly-doped semiconductor material such as polysilicon. Multiple components provided with such vias are then stacked and bonded together.

One critical step in the TSV process is via formation, in which a pattern of contacts is etched into the silicon. In order to maintain the required via quality, it is essential to control both the depth and profile of the vias.

GENERAL DESCRIPTION

There is a need in the art for a novel technique for monitoring parameters of pattern features produced during a TSV fabrication process, i.e. the depth and profile of the vias being created.

TSV are created by deep silicon etch, yielding a vertical hole in the silicon with high aspect ratio. TSV can have different cross sections, depending on the specific intended application and integration scheme, and can have circular, square, octagonal or annular shapes. Typical cross section sizes of the via (via diameters) are in the range of 1-50 μm, and depths are up to 200 μm, providing aspect ratios up to 20:1.

Figure 1:
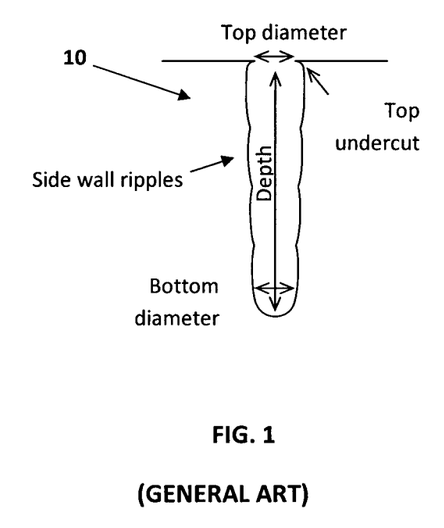
FIG. 1 schematically illustrates a typical via sectional view showing such parameters as top diameter, bottom diameter, depth, and sidewall ripples.

To ensure reliable and repeatable integration process, several crucial via profile parameters require monitoring and control such parameters as the via depth, top diameter, sidewall angle, side wall ripples (i.e. an oscillatory indent pattern appearing on the via walls as a result of the TSV fabrication process), bottom diameter and top undercut. In this connection, reference is made to FIG. 1 schematically illustrating a via profile 10. As shown, the via is typically defined by its top diameter, bottom diameter, depth, and sidewall ripples, see above. The via depth should exceed the final planned thickness of the layer in the chip stack, so that after thinning the wafer, it will form a connection between the two sides of the chip. The sidewall ripples should be reduced as much as possible to provide a substantially smooth side wall profile. "Smooth" via's side walls are required to ensure optimal filling of the via. The top and bottom diameters usually define a side wall angle. The coating and filling processes of the TSV, in following fabrication steps, require side walls of well-controlled angle. In addition, in order to guarantee good conductive properties of interconnect, significant bottom diameters must be maintained. In other words, the side-wall slope is needed to be kept very close to vertical. A possible consequence of the etching process is the creation of an undercut at the top edge of the via (top undercut). Such undercut may impair the following filling process.

Additional parameters of interest relate to coating or other processes done following the formation of the via which form thin layers on the via wall. In all cases, there is a need in the industry to control the thickness of these layers, hence to measure them.

Generally, the via top-diameter can be determined using several known techniques, including for example bright-field optical imaging, in which light is normally incident on the via region and specularly reflected light is detected and analyzed. However, such normal-incidence bright-file imaging cannot be used for information on the via depth for vias with large aspect ratios which is typical for TSV.

Other common approaches that have been suggested for the via depth determination are based on interferometric methods. Characterization of the other parameters of a via profile is significantly more challenging, since the signal reflected from the side-walls is considerably weaker than the signal reflected from the top surface and the via bottom, due to their sharp angles with respect to the incident light.

The present invention provides an optical technique for measurement of various parameters of the via profile, based on the general principle of dark field optical measurement. This approach provides for eliminating or at least significantly reducing the contribution arising from the top surface, as well as from the flat via bottom. The resulting signal is determined mainly and preferably solely by sidewall characteristics, and comparison of the measured signal to appropriate models can be used to extract the via parameters of interest.

In the fabrication process of the TSV, the via is formed by etching, and then a thin insulating layer (called a 'liner') is placed inside the via. This step is followed by growth of another layer ('barrier') that limits the diffusion of Cu atoms, and then by the growth of a thin metallic layer, called a 'seed', intended to improve the deposition process of the copper, making up the contact. Characterization of all these thin layers is of great industrial interest, as small defects, inhomogeneities and gaps can impair the TSV functionality.

The technique of the present invention is based on the use of dark field approaches, and allows "isolation" of light that is reflected from these layers and light reflected from the wafer surface. Comparison of the measured signal with simulated or reference (measured on known test structures) signals can allow characterization of the thin layers created on the via walls.

The measurement technique of the present invention can be implemented either for an isolated structure or a lattice of similar elements.

Thus, according to one broad aspect of the invention, there is provided an optical system for use in measuring in patterned structures having vias, the system being configured and operable to enable measurement of a via profile parameters, the system comprising an illumination channel for propagating illuminated light onto the structure being measured, a detection channel for collecting light returned from the illuminated structure to a detection unit, and a modulating assembly configured and operable for implementing a dark-field detection mode by carrying out at least one of the following: affecting at least one parameter of light propagating along both the illumination and detection channels, and affecting propagation of light along at least the detection channel.

In some embodiments of the invention, the modulating assembly is configured and operable for affecting at least polarization of light passing along the illumination and detection channels. The modulating assembly may comprise first and second polarizers accommodated in the illumination and detection channels and having substantially perpendicular planes of polarization. In another example, the modulating assembly comprises first and second polarizers accommodated in the illumination and detection channels respectively and having substantially parallel planes of polarization, and a common phase retarder accommodated in the illumination and detection channels. The phase retarder is located upstream of the second polarizer with respect to a direction of propagation of returned light from the structure along the detection channel. In yet another example, the modulating assembly comprises a common polarizer and a common phase retarder accommodated in a spaced-apart relationship in a common portion of the illumination and detection channels. The polarizer is located upstream of the phase retarder with respect to a direction of propagation of the illuminating light to the structure along the illumination channel.

Additionally or alternatively, the modulating assembly may be configured and operable for partial masking of both the illumination and detection channels. Such modulating assembly may comprise a single pattern formed by regions of different light transmission with respect to light used in the system, said pattern being located in a plane intersecting the illumination and detection channels in the vicinity of the system back focal plane or a plane conjugate to it, i.e. near or at the system back focal plane or a plane conjugate to it. The pattern may be in the form of a half-plane, restricting the directions of incident illumination, and blocking the radiation reflected specularly from these incident directions. In another example, the modulating assembly comprises first and second complementary patterns, each pattern being formed by regions of different light transmission with respect to light used in the system, the first and second patterns being located in conjugate planes in or close to the back focal planes of respectively the illumination and detection channels. For example, the first pattern in the illumination channel is in the form of two concentric rings, where a central ring defines a light transmitting region and a peripheral ring defines a light blocking region, and the second pattern in the detection channel is in the form of two concentric rings with a central ring defining a light blocking region and a peripheral ring defining a light transmitting region.

The system may also include a control unit configured and operable for receiving data indicative of detected light, and processing said data to determine at least one parameter of the via.

The measurements could be performed using a fitting procedure. According to this procedure, theoretical model describing a structure under measurements is used to generate theoretical data or reference data, and the latter is iteratively compared to measured data, while varying the model parameters until the "best fit" is found. The parameters of the "best fit" model are considered as corresponding to the measured parameters. Reference data could be also produced using test samples with known parameters.

The system may comprise an additional detection channel for collecting light specularly reflected from the structure.

According to yet another broad aspect of the invention, there is provided a method for use in optical measurements in patterned structures having vias for determining one or more via profile parameters, the method comprising applying a dark-field detection mode to the patterned structure under measurements by carrying out at least one of the following: affecting at least one parameter of light propagating along illumination and detection channels, and affecting propagation of light along at least the detection channel.

BRIEF DESCRIPTION OF THE DRAWINGS

In order to understand the invention and to see how it may be carried out in practice, embodiments will now be described, by way of non-limiting example only, with reference to the accompanying drawings, in which same reference numerals are used to identify elements or acts with the same or similar functionality, and in which.

It is noted that the embodiments exemplified in the figures are not intended to be in scale and are in diagram form to facilitate ease of understanding and description.

DETAILED DESCRIPTION OF EMBODIMENTS

FIG. 1 schematically illustrates a typical via profile defining such parameters as top diameter, bottom diameter, depth, and sidewall ripples.

As indicated above, the present invention provides for via profile monitoring technique by monitoring the above parameters, utilizing the dark-field approach according to which illumination and detection light propagation schemes are different in the accommodation of illumination and detection channels and/or parameters of illuminating and detected light.

The following are several examples of the system of the present invention for use in measuring the via profile parameters. To facilitate understanding, the same reference numbers are used for identifying components that are common in all the examples. Each of the measurement systems shown in these examples defines illumination and detection channels $C_1$ and $C_2$, and is configured to implement the dark-field mode by affecting at least one parameter of light propagating along illumination and/or detection channels, and/or affecting propagation of light propagating along at least the detection channel, and/or appropriate relative accommodation of the illumination and detection channel. These configurations provide for eliminating or at least significantly reducing detection of specularly reflected light by a dark-field detection unit.

Figure 2:
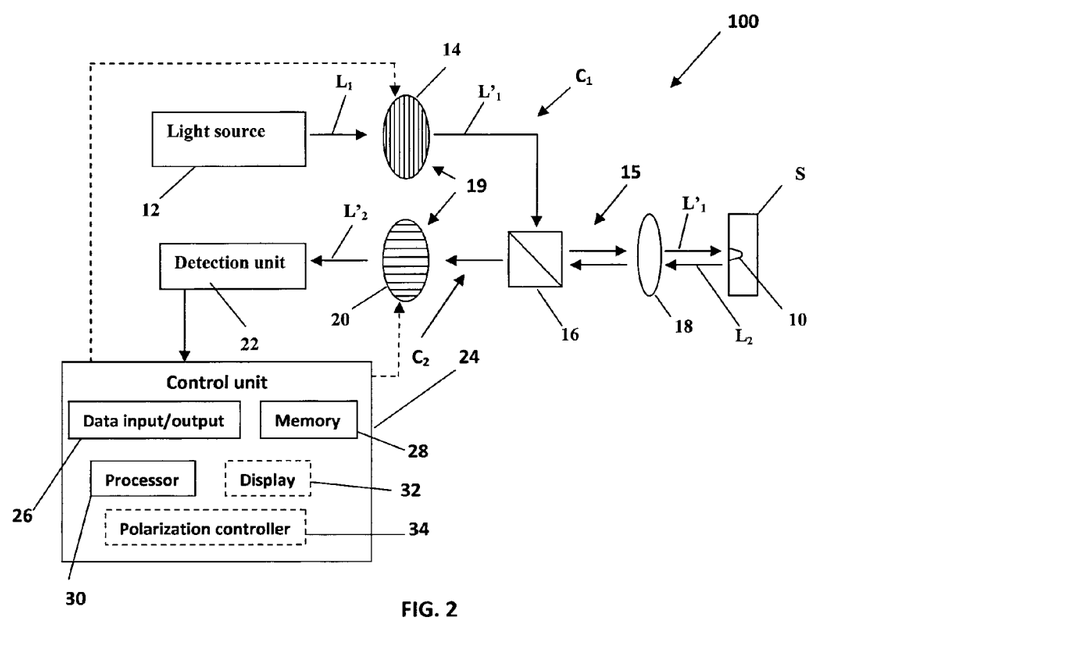
FIGS. 2, 3 and 4 show schematically three examples, respectively, of a measurement system of the invention utilizing a dark field setup configured for affecting polarization of light propagating in illumination and detection channels.
Figure 3:
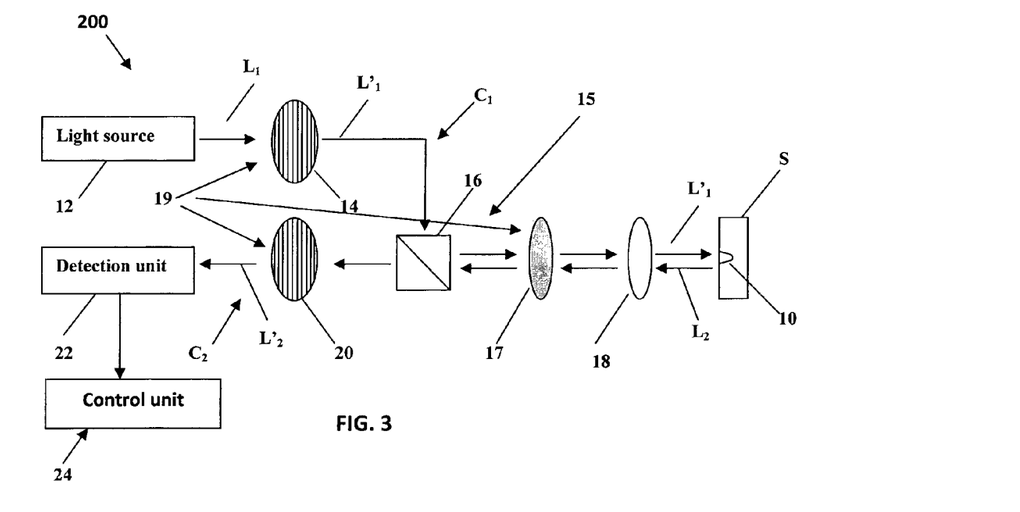
Figure 4:
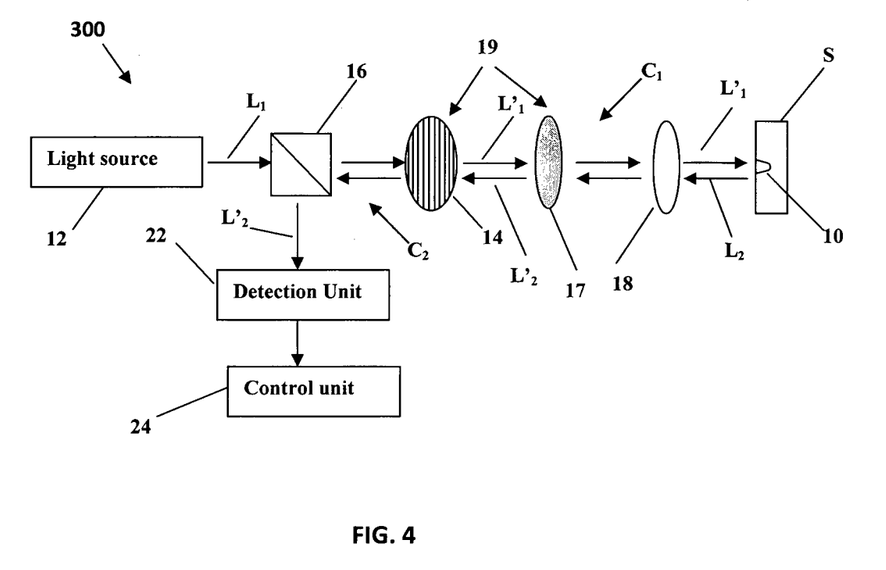

In the examples of FIGS. 2, 3 and 4, the system configuration is based on the understanding that light incident perpendicularly onto the top wafer surface and reflected specularly therefrom maintains its original polarization. Accordingly, it is possible to differentiate between light reflected from the top surface, and light reflected from surfaces having an oblique angle with respect to the incident direction.

FIG. 2 shows an optical dark-field measurement system 100 configured as a dark-field reflectometer for measuring in a sample S having a via 10. The system 100 defines illumination and detection channels $C_1$ and $C_2$, and is configured to implement the dark-field mode by affecting at least one parameter of light propagating along illumination and/or detection channels. The system 100 includes a light source unit 12 (which may be constituted by a light emitting arrangement or by a light guiding unit associated with an external light emitter), a detection unit 22, a light directing arrangement 15, and a light modulating assembly 19. In the present example, the system 100 is configured to provide mutually perpendicular polarizations for the incident and returned light channels $C_1$ and $C_2$. This is a so-called cross-polarized reflectometer. The light modulating assembly 19 includes polarizers 14 and 20 having fixed or controllable substantially perpendicular planes of preferred polarization. The light directing arrangement 15 includes a beam splitter 16 and focusing optics (objective) 18, and is accommodated in a common portion of the illumination and detection channels $C_1$ and $C_2$.

Also provided in the system 100 is a control unit 24, which is connectable to the output of the detector 22 (via wires or wireless signal transmission) for receiving and analyzing data indicative of the detected light. The control unit 24 is typically a computer system including such functional utilities as data input and output utilities 26, memory 28, processor 30 and possibly also a display 32. The control unit 24 may also include a polarization controller 34 in case at least one of the polarizers is a tunable device for selectively varying the orientation of its plane of polarization.

Light $L_1$ coming from the light source 12 propagates along the illumination channel $C_1$, and is polarized by the incident-path polarizer 14, and resulting polarized light $L'_1$ is directed onto the sample S by the beam splitter 16 which reflects it towards objective 18 that focuses light onto an illuminating region on the sample S. Light $L_2$ reflected (returned) from the illuminated region propagates along the detection channel $C_2$ being focused by optics 18 onto the beam splitter 16 and transmitted thereby to the polarizer 20. The so-polarized light $L'_2$ propagates to the detection unit 22.

In light $L'_2$ emerging from the polarizer 20, reflected contribution from surfaces perpendicular to the incident light direction is ideally completely suppressed. However, light components reflected from surfaces having an oblique angle with respect to the incident light propagation direction, such as the light components returned from the side walls of the via 10, can undergo significant polarization change, allowing at least part thereof to be collected by the detector 22.

FIG. 3 shows a measurement system 200 which distinguishes from the above-described crossed-polarizer dark field setup of FIG. 2 in that system 200 uses a phase retarder element. Here, a light modulating assembly 19 includes polarizers 14 and 20 having substantially parallel planes of preferred polarization and a phase retarder 17.

Light $L_1$ from a light source 12 passes through a polarizer 14, and polarized light $L'_1$ is reflected by a beam splitter 16 onto a phase retarder 17 which rotates the light polarization by $\theta=45°$, and the so-produced light $L''_1$ is focused by objective $L_1$ onto the sample. Returned (reflected) light $L_2$ is focused by lens unit 18 onto the phase retarder 17, and its phase is again rotated by 45°, resulting in light $L'_2$ which then passes the polarizer 20 in the detection path $C_2$, which has preferred plane of polarization oriented in parallel to that of incident path polarizer 14. Thus, light specularly reflected from the surface arrives at the second polarizer 20 at a perpendicular polarization, and is completely blocked. Light components of the returned light having their polarization rotated by an oblique reflection from the via walls can pass through the second polarizer and the resulting signal can be compared to simulated or reference (measured on known test structures) signals to extract information on the via profile.

FIG. 4 shows a system 300 which is configured generally similar to that of FIG. 3, i.e. eliminating specularly reflected light from the wafer surface using the polarization property, but in which a light modulating assembly 19 includes a single polarizer 14 and a phase retarder 17, and the polarizer 14 is located between the beam splitter 16 and the phase retarder 17. Such configuration provides the same optical performance but at a lower cost and with a reduced alignment requirements (e.g. between the polarizer and the beam splitter).

In the above-described examples of FIGS. 2-4, the dark-field approach utilized detection of light returned from the sample and propagating along the detection path having azimuth and elevation of the specular reflection but having different light parameters as compared to those of the illuminating light (i.e. different polarization) thus enabling to identify (detect) light returned from the side walls if the via.

In some other embodiments, dark field measurements are based on affecting light propagation through the illumination and detection paths such that only a part of the detection path having azimuth and elevation different from that of the specular reflection is connected to the detection unit. This can be achieved by using a so-called masked light-path. In this approach, a dark-field measurement is obtained by partial masking the detection light path at or near the back focal plane, and effectively preventing any light component specularly reflected from the top surface of the sample to be collected.

The above can be implemented using a mask in the common optical path (illumination and detection path). According to this technique, a masking element is placed upstream of the focusing optics with respect to the incident light propagation direction, limiting the illuminated regions on the objective and consequently the range of angles that are incident upon the sample. Similarly, such mask partially blocks the return light, limiting the acceptable reflected rays at the detector. This method is based on ascertaining that for every transparent point on the mask, the conjugate point (corresponding to the location to which the ray is reflected) is opaque.

Figure 5A:
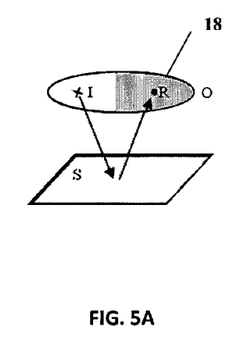
FIGS. 5A and 5B exemplify the technique of the invention where a dark field detection mode is achieved by affecting propagation of light through the illumination and detection channels, using a common pattern in the illumination and detection channels.
Figure 5B:
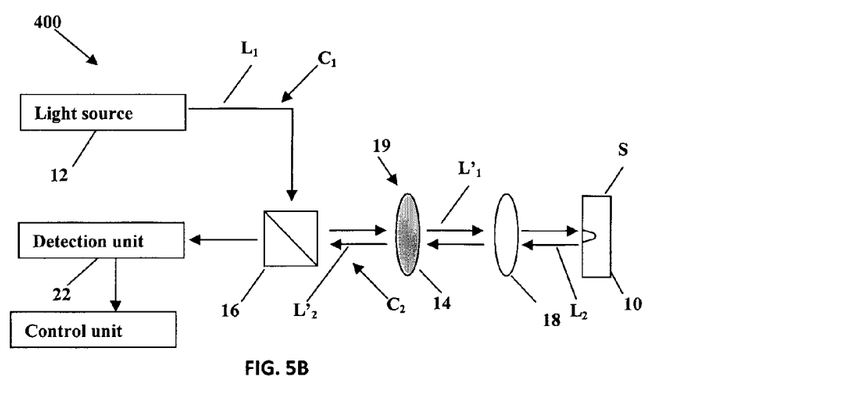

An example of such technique is presented in FIGS. 5A and 5B. As shown in FIG. 5A, if half of the objective lens 18 is rendered opaque, incident light ray I is specularly reflected from a flat surface S into a point R in the opaque half of the aperture, and is thus blocked. Only rays having their propagation direction altered by the sample (i.e. propagates with angles outside the propagation direction of the specular reflection) can be collected, implementing a dark field measurement. In other words, a mask located in the common illumination and detection path can be appropriately designed to block the zero-order diffraction and thus implement the dark-field detection mode.

FIG. 5B shows a measuring system 400 configured to implement the above-described masked light-path scheme. Light $L_1$ from a light source 12 is directed onto the sample along the illumination path $C_1$ and is reflected by a beam splitter 16 onto a partially blocking mask 14 and then is focused by objective 18 onto the sample S. Light returned from the illuminated sample is collected by objective 18 and focused onto the mask 14, and then transmitted by the beam splitter 16 to the detection unit 22.

Figure 6A:
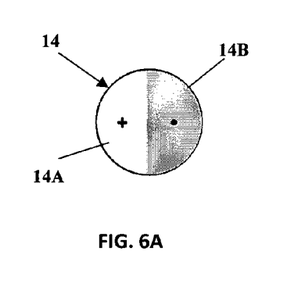
FIGS. 6A and 6B show examples of the designs for light-path mask suitable to be used in the system of FIG. 5B.
Figure 6B:
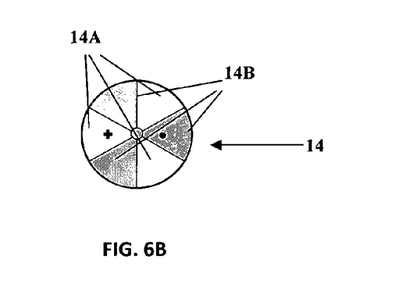

Reference is made to FIGS. 6A and 6B showing specific but not limiting examples of the designs for light-path mask suitable to be used in the system of FIG. 5B to implement dark-field measurement.

In the example of FIG. 6A, the mask 14 has two halves one being transparent and the other opaque for the light used in the system, and is to be placed with respect to the objective lens so as to block a half of the numerical aperture (as shown FIG. 5A). The mask is preferably designed to cover slightly more than half of the objective area, to guarantee that no rays leak through the mask in the central region of the field of view. The mask of FIG. 6A is simple to implement, but it strongly breaks the left-right symmetry, possibly leading to unwanted effects. For example, such symmetry breaking may cause different sensitivity to objects oriented in the horizontal or vertical direction. Such effects may be reduced to some degree by using a mask in which the field is divided into more than 2 parts, e.g. 6 parts, as exemplified in FIG. 6B. Here, again, the specular reflection from the surface is completely eliminated, as any transparent region in the incident path is conjugated by a masked region at the return path. The central region in the mask is rendered opaque, in order to prevent bright-field contributions from the field center.

More elaborate designs based on the same approach as in FIG. 6B can be considered, in which the field is divided into 2n wedges, with n being an odd number (so that it is possible to have pairs of opposing transparent and blocked parts). Such designs are advantageous in terms of rotational symmetry, but may be harder to manufacture and are limited in the requirement that each transparent part must be considerably wider than the wavelength, to avoid diffraction effects.

It should be understood that the mask of any appropriate design generally presents a pattern of regions of different transmission with respect to light incident thereon. Such a pattern may ne constituted by physical patterned structure or by an electronic pattern (such as spatial light modulator, e.g. LC panel).

In the above example of FIG. 5B, a mask is located in the common optical path. As indicated above, when using a single mask to control the allowed light paths, the measurement system breaks the rotational symmetry, and may lead to unwanted artifacts. Alternatively, separate masking of the allowed light paths in the incident and reflected optical paths can be utilized by placing complementary masks in the illumination and collection paths. This is exemplified in FIG. 7 showing a measurement system 500 which is configured generally similar to the above-described system 100 (FIG. 2) but in which different polarizers in the illumination and collection paths $C_1$ and $C_2$ are replaced by different illumination and collection patterns (masks) at or near the back focal plane 14 and 20.

Figure 7:
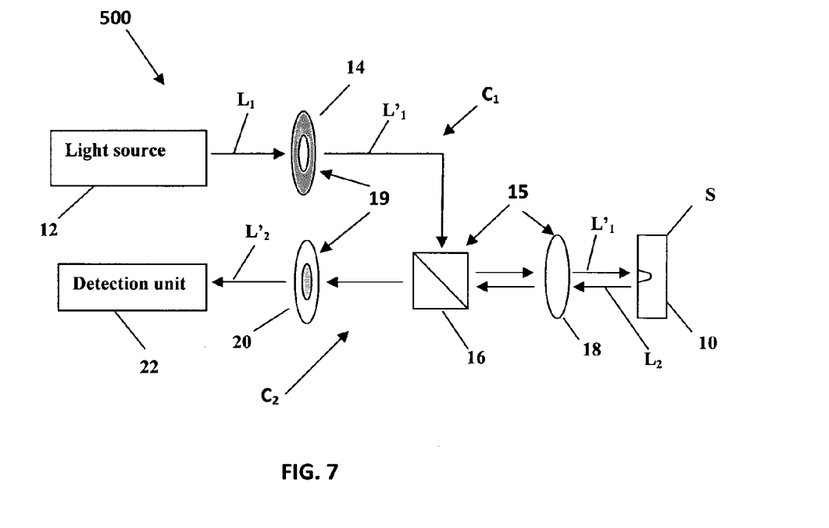
FIG. 7 exemplify the technique of the invention where a dark field detection mode is achieved by affecting propagation of light through the illumination and detection channels, by placing complementary masks in the illumination and collection channels.

As shown in FIG. 7, light $L_1$ from the light source 12 passes through the illumination mask 14, and light portion $L'_1$ transmitted through the central region of the mask 14 is directed onto the sample S by the beam splitter 16 and objective 18. Reflected light $L_2$ is collected by the objective 18 and transmitted by beam splitter 16 onto the collection mask 20. Light portion $L'_2$ that passes through the transparent periphery region of the mask 20 is detected by the detector 22. In this implementation, the incident light path is partially blocked by the mask 14, leaving a circular transparent region in the center of the field. A conjugate mask 20, blocking the central circular region is used in the reflected light path $C_2$, so that light specularly reflected from the sample flat horizontal surfaces is blocked and only light that was diffracted by the via side walls is collected. Again, in order to avoid bright-field contribution, the masks are designed to have an overlap. Contrary to the methods based on a single mask described above, in this approach the cylindrical symmetry is maintained. However, this advantage is contrasted by the additional complexity in implementation, caused by the use of two different elements and requiring accurate alignment.

Yet another technique facilitating measurement of the via profile parameters by detection the response from the side walls of the via utilizes dark field measurement based on separate illumination and collection paths. In this approach, a dark field measurement is implemented by illuminating the sample in one direction, and placing a detector at an orientation that does not collect light specularly reflected from the surface. A possible improvement to this approach is by scanning the illumination \ detection directions, to obtain more information on the via profile.

Figure 8A:
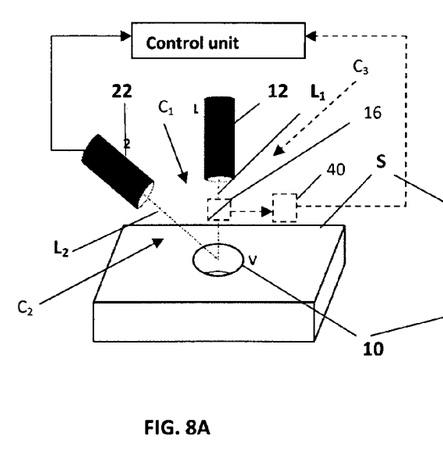
FIGS. 8A-8C exemplify systems of the invention where a dark field detection mode is achieved by spatially separating the illumination and detection channels by using different azimuth and elevation for the illumination and detection channels.
Figure 8B:
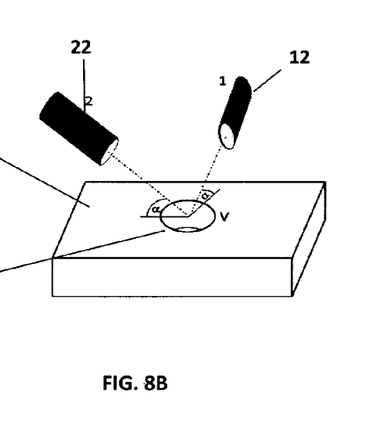
Figure 8C:
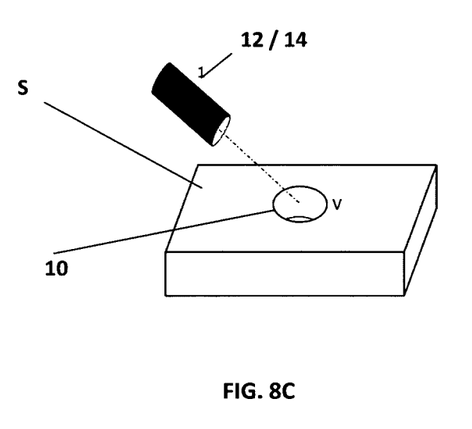

According to one possible example of this embodiment, one oblique and one normal channels can be used. Here, the illumination is incident on the via in the normal direction and a separate detector is placed at an oblique angle, or vice versa. Reference is made to FIGS. 8A-8C showing three examples respectively for dark-field setup, where orientations of incident and collected light are separate.

As shown in FIG. 8A, light $L_1$ coming from a light source 12 is incident perpendicular to the wafer surface S and light $L_2$ to be detected by detection unit 14 is collected in an oblique angle. This configuration can be reversed, so that light is incident in an oblique angle and collected in perpendicular to the surface. This way, only light diffracted by the via can be collected by the detector. This design has the advantage that the normal channel, common to many other applications, can be used for bright field measurements.

According to another example, two oblique channels are used. For high aspect-ratio vias, light incident at an angle a with respect to the surface is scattered in all azimuths, but predominantly in the same angle a. This behavior favors using a dark field measurement in which light is incident and collected at the same angle a with respect to the surface, but at different azimuths, so that light specularly reflected from the surface is not collected. FIG. 8B presents such approach. When compared to the example of FIG. 8A, the configuration of FIG. 8B provides significantly stronger signal.

According to yet another example, a single oblique illumination and collection path can be used. As shown in FIG. 8C, light is incident on the via at an oblique angle, and collected at the same direction. In this case, the same oblique path is used for illumination and collection, possibly simplifying the implementation.

The measurement technique of the invention can be used in conjunction with standard bright-field reflectometry. This is exemplified in FIG. 8A, where the bright-field channel $C_3$ is illustrated by dashed lines including a beam splitter 16 and possibly collection optics (not shown), and a detection unit 40. Light specularly reflected from the sample and propagating along a path, which in the case of normal incidence substantially coincides with the illumination path, is reflected by the beam splitter 16 to the detector 40. A control unit 24 may be configured for selectively switching between the dark- and bright-field modes.

It should be understood that the combined "dark-field" and bright-field system of the invention is not limited to this specific example of FIG. 8A, and it would be clear for person skilled in the art that any of the above described dark-field systems can be easily modified to include the bright-field channel as well.

In such a combined system utilizing both the bright-field and dark-field channels, standard reflectometry can be used to obtain a reflectometry signal (spectrum) from the top surface alone (without the via hole) using the bright-field channel. This measured reflectometry signal can be analyzed to obtain the characteristic dimensions of several components in the probed structure, for example the thickness of masking layers used for the patterning process. Then, dark field reflectometry measurements are taken (using any of the above described techniques). The analysis of the dark field data can benefit from injection of parameter values obtained from the standard bright field measurement, resulting in a more accurate profile measurement. Alternatively, data from both bright-field and dark-field measurements can be concurrently analyzed to deduce geometrical properties of the measured structure that cannot be obtained by either of these measurements separately.

Also, it should be understood that combined system based on eliminating specularly reflected light from the wafer surface using the polarization and masking and/or other technique as described above could be used.

Also, it should be noted the measurements taken with the technique of the invention are dependent on the numerical aperture of the system. In high aspect-ratio structures, a strong sensitivity is expected between the direction of incident and reflected radiation. Additional information on the probed structure geometry can be obtained by modifying the system numerical aperture (NA) and measuring the effect on the detected signal at several NA configurations, which can for example be achieved by scanning across the NA, incidence angle, etc.

One can obtain several different dark-field signals from a single via, even when utilizing the same measurement approach. For example, by focusing the measurement spot on different locations on the via (e.g. not on the via center), the interaction of light with the via will change, and the reflected signal will be altered. This added information can then be used to improve the accuracy of the profile characterization. For vias which are not cylindrically symmetric, rotating the via with respect to the measurement system will also change the reflected signal, thereby yielding additional information on the via profile. In this case, dark-field measurements can be taken for several rotations and translations of the via, providing multiple datasets, dependent on the via profile.

Most of the methods described above implement a setup which by itself creates a measurement spot which is not invariant under rotations (e.g., due to the direction defined by polarization, by the mask applied to the NA or by the direction of the incident\collected light). In all these cases, one can obtain multiple dark-field measurements from a via by measuring at a location other than the via center, and rotating the component that breaks the rotation symmetry. For example, when using a crossed-polarizers setup, one can center the optical system at a location shifted from the via center, and measure the dark-field signal for different orientations of incident polarization (keeping, at all times, the orientation of the second polarizer perpendicular to the first). Alternatively, when using a masked light path, one can rotate the mask. When measuring a via which is not cylindrically symmetric, one can obtain different dark-field signals in this way even when measuring at the via center.

It should also be noted that the system of the invention can be configured to concurrently use any combination of the above-described examples. It is possible to use a measurement scheme in which two of the above methods are used in conjunction. For example, it is possible to use crossed-polarization alongside masked light-path. This approach will allow greatly improved elimination of reflections from the top surface, and better isolation of the signal reflected from the via side walls.

Alternatively, more than one of the above described techniques can be used sequentially, e.g. to obtain several sets of independent information. This approach can also allow improved flexibility in selection of the most suitable measurement technique to characterize vias of different shapes.

As indicated above, the dark-field measurement technique of the invention can be used for monitoring various via profile parameters. The dark-field techniques described above can be used as the basis for reflectometry measurements of the via. In these measurements, a broad spectrum light is incident upon the via, and the wavelength-dependent reflection is measured. The reflected amplitude at each wavelength is determined by interference properties of light reflected from the different parts of the exposed wafer.

In order to deduce the via profile parameters, a comparison can be made between the measured reflection spectrum and a set of calculated spectra from via with different profile parameters. Then, the via profile that produces the best-fit calculated spectrum to the measurement can be identified. The dark field measurements provide high sensitivity of the measured spectrum to the profile parameters, since essentially all the measured radiation originates from reflection from the via walls.

Calculation of the reflected spectrum can be attained using a multitude of analytical and numerical approaches. For simple via structures, the Maxwell equations can be analytically solved, so that the reflected field can be directly deduced given the incident field. When considering more complicated via structures, various numerical methods can be used. A relatively simple approach is the ray-tracing (geometrical) approximation, which is accurate as long as the modeled structure is large as compared to the wavelength of light used in the measurement system. When this assumption is not valid, more accurate numerical methods are required. Commonly used methods are finite elements approaches, such as finite-difference time domain (FDTD) calculations, expansion of the scattering object as a sum of some basis set of shapes, such as the T-matrix or multipole expansion, eigenvalue decomposition and many more.

Figure 9:
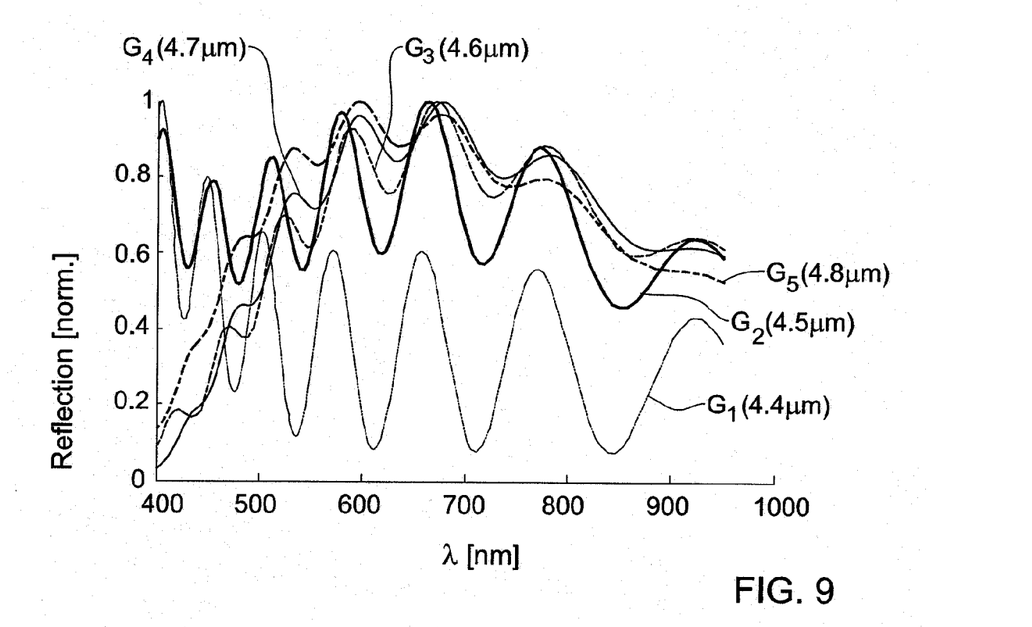
FIGS. 9 and 10 exemplify ray-tracing calculation for the reflected spectrum from a circular-shape via in a crossed-polarizers setup of FIG. 2, for different radii of the bottom of the via.

Reference is made to FIG. 9 exemplifying ray-tracing calculation for the reflected spectrum from a circular-shape via of 5 μm radius, 60 μm depth and bottom curvature of 6 μm, for varying values of bottom radius, in a crossed-polarizers setup (similar to that of FIG. 2). The calculations were made using a ray-tracing model. Here, five graphs are shown $G_1$-$G_5$ corresponding to calculated reflected spectrum, for different bottom radii of 4.4 µm, 4.5 µm, 4.6 µm, 4.7 µm and 4.8 µm respectively. The inventors have found that changes of 100 nm in the bottom radius lead to significant changes in the expected spectrum, providing good sensitivity of the measured spectrum to this profile parameter.

Figure 10:
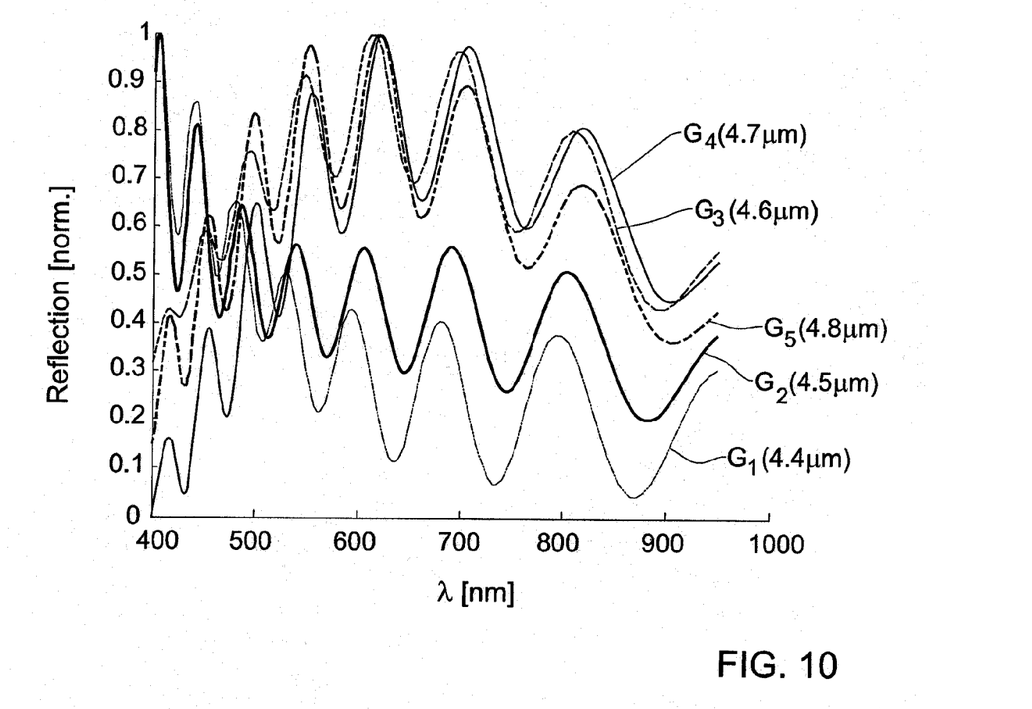

A similar calculation for a half-masked light path (FIG. 5B with the mask design of FIG. 5A) is presented in FIG. 10 for a circular-shape via of 5 µm radius, 60 µm depth and bottom curvature of 6 µm, and varying bottom radius. Similarly, significant sensitivity is predicted for the dependence of the measured spectrum on the bottom via radius, which indicates that this method is similarly effective in deducing this parameter.

Thus, the present invention provides an effective and simple technique for measuring the via profile parameters in patterned structures. The invention utilizes a dark-field detection mode, which may if needed be used in combination with an additional bright field detection mode. The dark-field mode is implemented by affecting one or more parameters/conditions of both the illumination or detection light, and/or affecting propagation path of light propagating along at least the detection channel, and/or appropriate relative accommodation of the illumination and detection channel, all aimed at eliminating or at least significantly reducing detection of specularly reflected light by the dark-field detection unit.

Those skilled in the art will readily appreciate that various modifications and changes can be applied to the embodiments of the invention hereinbefore described without departing from its scope defined in and by the appended claims.

The invention claimed is:

1. A method for use in optical measurements in patterned structures having vias the method comprising:
   applying a dark-field detection mode to the patterned structure under measurements by carrying out the following:
   illuminating the structure with light of a broad spectrum of wavelengths such that the patterned structure is larger than the largest wavelength of the illuminating light, said light having a predetermined polarization state and propagating onto the structure with normal incidence;
   detecting light returned from the illuminated structure, while providing mutually perpendicular polarizations for the incident and the returned light;
   processing measured spectral data indicative of the detected light, said processing comprising applying a model and determining one or more of the following parameters of side walls of the via: a sidewall angle, side wall ripples, and characteristics of a thin insulating layer created on the via walls.

2. The method of claim 1, wherein said providing mutually perpendicular polarizations for the incident and the returned light comprises passing light propagating through the illumination and detection channels through first and second polarizers respectively accommodated having substantially parallel planes of polarization, and through a common phase retarder accommodated in the illumination and detection channels, the phase retarder being located upstream of the second polarizer with respect to a direction of propagation of returned light from the structure along the detection channel.

3. The method of claim 1, wherein said providing mutually perpendicular polarizations for the incident and the returned light comprises passing illuminated light and light returned from the structure through a common polarizer and a common phase retarder accommodated in a spaced-apart relationship in a common portion of the illumination and detection channels, the polarizer being located upstream of the phase retarder with respect to a direction of propagation of the illuminating light to the structure along the illumination channel.

4. The method of claim 1 further comprising receiving measured data indicative of detected light.

5. The method of claim 1, wherein said processing comprises carrying out a fitting procedure utilizing iterative comparison between theoretical data or reference data corresponding to data indicative of detected light from a structure similar to the structure under measurements until best fit is found.

6. The method of claim 1, further comprising determining a via depth, a top diameter of the via.

7. The method of claim 6, further comprising determining parameters of seed layer.

8. The method of claim 1, wherein the illuminating and/or detecting is performed at a plurality of numerical aperture configurations.

9. The method of claim 1, further comprising focusing the measurement spot on different locations on the via so that the interaction of light with the via changes and the reflected signal is altered.

10. The method of claim 1, further comprising measuring the dark-field signal for different orientations of incident polarization.

11. The method of claim 1, wherein said selected model uses a ray-tracing geometrical approximation.

12. The method of claim 6, wherein said selected model uses a ray-tracing geometrical approximation.

13. The method of claim 7, wherein said selected model uses a ray-tracing geometrical approximation.

14. The method of claim 8, wherein said selected model uses a ray-tracing geometrical approximation.

15. The method of claim 10, wherein said selected model uses a ray-tracing geometrical approximation.

* * * * *